United States Patent [19]

McGill

[11] 4,382,038

[45] May 3, 1983

[54] HYDROCYANATION OF OLEFINS

[75] Inventor: Robert N. McGill, Orange, Tex.

[73] Assignee: E. I. Du Pont de Nemours and Company, Wilmington, Del.

[21] Appl. No.: 307,649

[22] Filed: Oct. 1, 1981

[51] Int. Cl.³ .................. C07C 120/02; C07C 121/26
[52] U.S. Cl. ............................................. 260/465.8 R
[58] Field of Search ................................ 260/465.8 R

[56] References Cited

U.S. PATENT DOCUMENTS

| | | | |
|---|---|---|---|
| 3,496,217 | 2/1970 | Drinkard, Jr. et al. | 260/465.3 |
| 3,496,218 | 2/1970 | Drinkard, Jr. | 260/465.3 |
| 3,766,237 | 10/1973 | Chia et al. | 260/465.3 |
| 3,903,120 | 9/1975 | Shook, Jr. et al. | 260/439 R |
| 4,082,811 | 4/1978 | Shook, Jr. | 260/465.8 R X |

Primary Examiner—Joseph Paul Brust

[57] ABSTRACT

Unreacted hydrogen cyanide in the product from a hydrocyanation reactor is reduced while maintaining maximum yield to dinitriles.

7 Claims, No Drawings

HYDROCYANATION OF OLEFINS

BACKGROUND OF THE INVENTION

1. Field of the Invention

The present process is directed to the production of dinitriles and more particularly, to an improvement in the method of hydrocyanating 3- and/or 4-pentenenitriles in the presence of a zero-valent nickel catalyst to produce adiponitrile.

2. Description of the Prior Art

U.S. Pat. No. 3,496,218 issued on Feb. 17, 1970 describes in general terms a process for the preparation of dinitriles especially adiponitrile by the hydrocyanation of non-conjugated, ethylenically unsaturated organic compounds, e.g., 3- and/or 4-pentenenitriles using certain nickel complexes as catalysts. The catalysts are promoted by organoborane compounds such as triphenylborane. A wide range of process conditions and relative amounts and types of reactants are disclosed. Other operable promoters are described in U.S. Pat. No. 3,496,217 issued on Feb. 17, 1970.

A particularly useful form of zero-valent nickel catalyst is described in U.S. Pat. No. 3,766,237 issued on Oct. 16, 1973. The patentees disclose the use of an excess of the triarylphosphite ligand in the hydrocyanation along with the addition of certain ethers to improve the yield and increase the pounds of product which can be made per pound of catalyst consumed.

U.S. Pat. No. 4,082,811 issued on Apr. 4, 1978 discloses a hydrocyanation process coupled with a method for recovery of catalyst.

SUMMARY OF THE INVENTION

An improved process for the production of dinitriles, e.g., adiponitrile by the hydrocyanation of unsaturated nitriles, e.g., 3- and/or 4-pentenenitriles in the presence of a zero-valent nickel containing catalyst promoted for example, with an arylborane, i.e., triphenylborane in a primary reaction zone under mild reaction conditions as evidenced by a dinitrile product effluent from the primary zone having at least 1,000 and usually at least 2,500 ppm unreacted hydrogen cyanide therein comprising, or consisting essentially of, passing said effluent through a secondary zone in the absence of added hydrogen cyanide while maintaining the effluent at a temperature in the range of about 45°–85° C., preferably 50°–75° C. wherein the volume of the secondary zone is sufficient to reduce the hydrogen cyanide in the effluent from that zone to less than about 400 ppm which can be accomplished with a residence time in the range of about 5 minutes to 2 hours.

In one preferred mode of operation no catalyst or promoter is introduced into the secondary zone.

DETAILED DESCRIPTION OF THE INVENTION

Although the hydrocyanation reaction can employ any non-conjugated, ethylenically unsaturated organic nitrile having from 4 to 20 carbon atoms, it is of particular interest in the hydrocyanation of pentenenitriles, e.g., cis- and trans-3-pentenenitrile (3PN), 4-pentenenitrile (4PN) and mixtures thereof (3,4-PN's) to produce adiponitrile (ADN), an intermediate used in the production of hexamethylenediamine which in turn is used to produce polyhexamethyleneadipamide, a commercial polyamide useful in forming fibers, films and molded articles.

The preparation of zero-valent nickel Ni(O) catalyst which is used in the practice of the present invention is found in U.S. Pat. No. 3,903,120 issued on Sept. 2, 1975. The most attractive is a catalyst having the general formula $NiL_4$ where L is a neutral ligand such as a triarylphosphite of the formula $P(OAr)_3$ wherein Ar is an aryl group of up to 18 carbon atoms. Illustrative of the aryl groups are methoxyphenyl, tolyl, xylyl and phenyl. Meta- and para-tolyl and mixtures thereof are the preferred aryl groups. Excess ligand can be employed.

Preferred promoters which are used with the above-described catalyst are triarylboranes including those of the formula $BR_3$ wherein R is an aryl or substituted aryl group having 6 to 12 carbon atoms, e.g., phenyl, ortho-tolyl, para-tolyl, naphthyl, methoxyphenyl, biphenyl, chlorophenyl and bromophenyl. Triphenylborane (TPB) is preferred.

The design of the primary reaction zone, i.e., where hydrogen cyanide is added to the other reactants is not critical to the present invention. Preferably the primary zone comprises a plurality of stages in series with the product from one stage continuously directed to a subsequent stage and the hydrogen cyanide added to each stage.

It is preferred to conduct the hydrocyanation under mild conditions, e.g., at low temperature, i.e., about 45° C. to minimize yield loss and maximize catalyst and promoter utility. Under these mild conditions a significant amount of hydrogen cyanide is not reacted resulting in a product effluent from the primary reaction zone containing at least 1,000 and usually more than 2,500 ppm hydrogen cyanide. The upper limit on the unreacted hydrogen cyanide in the product from the primary reaction is governed by the requirement that the reaction reach steady state, i.e., where the concentration of hydrogen cyanide in the product effluent is constant with significant reaction occurring. The permissible upper limit can vary from system to system, but if exceeded, results in an increasing concentration of hydrogen cyanide in the product effluent with eventual loss of reaction.

The unreacted hydrogen cyanide in the product from the primary reaction zone can represent an economic and operational penalty. If the temperature of the product fluid is increased to a level necessary to effect separation of the various components by distillation, the hydrogen cyanide reacts with residual 3,4-PN's at the substantially increased temperature with resultant poor yield and, therefore, the overall yield decreases. Unreacted HCN causes problems in refining equipment by putting an excessive load on vacuum jets, e.g., and also by causing solids formation in the equipment due to polymerization of the HCN.

If the temperature in the primary reaction zone is increased to react more HCN and thereby reduce the level of HCN in the product, the overall yield is decreased. If reduction of hydrogen cyanide is attempted by increasing the activity and/or amount of catalyst, or promoter, the cost of catalyst and promoter and/or their recovery increases.

It has been discovered that by retaining the effluent from the primary reaction zone in a secondary zone where its temperature can be controlled and where no HCN is added to the effluent, the unreacted HCN can be reduced at a temperature where a severe yield penalty is not realized, i.e., a better overall yield is obtained as compared to the case where the stream is heated to a temperature necessary to effect separation of the components. This benefit is realized without increasing the level and/or activity of the catalyst and promoter in the primary reaction zone. This invention also takes advantage of the residual catalyst in the product effluent. The extent of the reduction in the level of hydrogen cyanide can be sufficient to minimize the other problems discussed hereinabove. Thus, the present invention permits operation of the primary hydrocyanation at desired conditions and minimizes the disadvantages of such conditions.

The design of the secondary zone is not critical, e.g., it can be either a continuous stirred tank reactor or a plug-flow reactor or any combination thereof equipped with suitable means for temperature control. Other designs are obvious to those skilled in the art.

The temperature in the secondary zone should be maintained in the range of 45°–85° C., preferably at least 10° C. higher than the temperature in the primary zone and in the range of 50°–75° C. One skilled in the art will appreciate that the size of the secondary zone required for substantial reduction in hydrogen cyanide varies inversely with the temperature maintained therein.

The following Example and Comparative are presented to illustrate but not to restrict the present invention and are directed to the hydrocyanation of 3-PN and/or 4-PN to produce ADN using Ni(O) catalyst containing a mixed m,p-tritolylphosphite ligand (TTP) with triphenylborane (TPB) as a promoter. It is understood that other types of nitriles and catalyst are contemplated. Parts and percentages are by weight unless otherwise noted.

EXAMPLE AND COMPARATIVE

A Ni(O) catalyst is prepared by reacting metallic powdered nickel and m,p-tritolylphosphite in the presence of phosphorus trichloride as a catalyst and 3,4-PN's as a solvent according to U.S. Pat. No. 3,903,120. This catalyst solution was mixed with a 17.5% solution of triphenylborane in refined 3,4-PN's in a 500 cc glass vessel equipped with an air driven turbine agitator to provide the feed mixture to the primary hydrocyanation zone.

The primary hydrocyanation zone consisted of two nine-liter glass reactors which were baffled and were agitated with flat blade agitators, driven by air motors. The effluent from the first reactor overflowed into the second reactor. The hydrogen cyanide reduction zone, or secondary zone, consisted of a 650 cc glass, baffled, mechanically agitated reactor which in the Example received feed as overflow from the second reactor in the primary zone. Individual proportional temperature controllers regulated hot water flow through internal heating coils in each reactor. Precautions were taken to exclude air from all vessels.

The system was started up filling the first reactor in the primary zone with feed mixture directed by overflow from feed mix vessel. When the first reactor was full, the temperature of the contents was increased to 41° C. When the temperature stabilized, inhibitor free, liquid HCN flow was introduced into the first reactor. The HCN was stored in a reservoir maintained at $-5°$ to $-10°$ C. to prevent polymerization. HCN was fed to each reactor in the primary zone using a variable stroke length piston pump and was added near the vessel agitator blades through a dip tube. When the second reactor was filled with the overflow from the first reactor, its contents were heated to 48° C. When the temperature of the second reactor stabilized, HCN was introduced, using a separate variable stroke length piston pump. When the HCN reduction zone reactor was filled with overflow from the second primary reactor the temperature of its contents was increased to 65° C. Temperatures of the second reactor and the HCN reduction zone were varied in steps to give unreacted HCN concentrations in the effluent from the reactors (primary and secondary) of 4,500 ppm and 400 ppm, respectively. Unreacted HCN was determined by infrared spectroscopy. Steady state operation at the conditions set forth in the Table was reached in 32 hours. During the following 18 hours samples were withdrawn every 3 hours from the feed mixing vessel, the second primary reactor, and the HCN reduction (secondary) zone. These samples were analyzed for PN's, DN's, TTP and Ni(O). The average results are reported in the Table.

For the comparative, which followed in time directly after the example, no changes were made in the conditions or feed to first reactor. The temperature of the second vessel was increased in steps until a steady state unreacted HCN concentration of 400 ppm in the effluent from this vessel was obtained. Approximately 12 hours were required to achieve this steady state. Samples were taken at 4 hour intervals for the next 16 hours from the second primary reactor and the feed mixing vessel. These samples were analyzed for PN's, DN's, TTP and NI(O). The average results are reported in the Table.

TABLE

| EXAMPLE NUMBER | FEED OVERALL MOL RATIO BASED UPON ONE MOL OF Ni (O) | | | | WEIGHT % Ni (O) | TEMPERATURE °C. BY STAGE | | HCN FEED SPLIT (% BY WEIGHT BY STAGE) | | OVERALL RATE GMS ADN/CC/MIN $\times 10^4$ |
|---|---|---|---|---|---|---|---|---|---|---|
| | TPB | TTP | 3,4-PN's | HCN | | 1st | 2nd | 1st | 2nd | |
| Comparative | 0.367 | 9.98 | 141 | 50.2 | .330 | 41 | 60 | 50 | 50 | 4.5 |
| Example | 0.367 | 9.98 | 141 | 50.2 | .330 | 41 | 47 | 50 | 50 | 4.5 |

| EXAMPLE NUMBER | REACTOR EFFLUENT | | HCN REDUCTION ZONE EFFLUENT | | | OVERALL AVERAGE TEMP. °C. | OVERALL YIELD ADN** % | HOLD-UP TIME IN REDUCTION ZONE (MINUTES) |
|---|---|---|---|---|---|---|---|---|
| | PPM HCN | % HCN REACTED | PPM HCN | TEMP °C. | % HCN REACTED | | | |
| Comparative | 400 | 99.5 | * | * | * | 51 | 90.7 | * |
| Example | 4500 | 94.1 | 400 | 72 | 99.5 | 46 | 91.6 | 22 |

*No reduction zone
**From 3-,4-PN

I claim:
1. An improved process for the production of dinitriles by the addition of hydrogen cyanide to pentenenitriles in the presence of a zero-valent nickel catalyst promoted with a triarylborane in a primary reaction zone under mild hydrocyanation conditions to produce a dinitrile product effluent from the primary zone having at least 1,000 ppm unreacted hydrogen cyanide therein, comprising passing said effluent and said catalyst through a secondary zone in the absence of added hydrogen cyanide while maintaining the effluent at a temperature in the range of about 45°–85° C. wherein the volume of the said secondary zone is sufficient to provide a residence time for the effluent of about 5 minutes to 2 hours.

2. The process of claim 1 wherein the effluent from the primary zone is maintained at a temperature in the range of 50°–75° C.

3. The process of claim 1 wherein no catalyst or promoter is added to the effluent while in the secondary zone.

4. The process of claim 2 wherein no catalyst or promoter is added to the effluent while in the secondary zone.

5. In a process for the production of dinitriles by reacting hydrogen cyanide with pentenenitriles in the presence of a zero-valent nickel catalyst and a triarylborane and wherein the reaction is conducted under conditions such that the concentration of unreacted hydrogen cyanide in the product effluent is at least 1,000 ppm, the improvement which comprises terminating the introduction of hydrogen cyanide and thereafter maintaining the reaction mixture at a temperature in the range of about 45°–85° C. in the presence of the initially charged catalyst until the concentration of unreacted hydrogen cyanide in the mixture is less than about 400 ppm.

6. The process of claim 5 wherein the reaction mixture is maintained at a temperature in the range 50°–75° C.

7. The process of claim 5 or 6 wherein no catalyst or promoter is added to the reaction mixture after the introduction of hydrogen cyanide is terminated.

* * * * *